United States Patent [19]

Briggs et al.

[11] Patent Number: 4,892,806

[45] Date of Patent: Jan. 9, 1990

[54] NON-IONIC SURFACE ACTIVE COMPOUNDS AND PHOTOGRAPHIC MATERIALS CONTAINING THEM

[75] Inventors: Catherine B. A. Briggs, Middlesex; Alan R. Pitt, Hertfordshire, both of England

[73] Assignee: Eastman Kodak Company, Rochester, N.Y.

[21] Appl. No.: 249,741

[22] Filed: Sep. 26, 1988

[30] Foreign Application Priority Data

Oct. 30, 1987 [GB] United Kingdom ................. 8725486

[51] Int. Cl.$^4$ .......................... G03C 1/04; G03C 1/38; G07C 103/07; G07C 103/10
[52] U.S. Cl. ..................................... 430/449; 430/512; 430/546; 430/637; 430/644; 430/935; 252/357; 564/152; 564/158; 564/159
[58] Field of Search ............... 430/637, 546, 449, 935, 430/644, 512; 564/158, 159, 152; 252/357

[56] References Cited

U.S. PATENT DOCUMENTS

| | | | |
|---|---|---|---|
| 2,653,932 | 9/1953 | Schwartz | 260/211 |
| 2,662,073 | 12/1953 | Mehltretter et al. | 260/102 |
| 2,958,665 | 11/1960 | Stefcik | 252/316 |
| 3,341,458 | 9/1967 | Mayhew | 252/117 |

OTHER PUBLICATIONS

Research Disclosure, Dec. 1978, #17643, pp. 22–31; "Photographic Silver Halide Emulsions, Preparations, Addenda, Processing and Systems".

Primary Examiner—Richard L. Schilling
Attorney, Agent, or Firm—Paul A. Leipold

[57] ABSTRACT

The invention provides water soluble surface active compounds having the formula

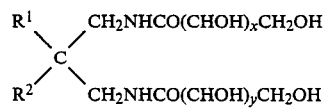

wherein
each of $R^1$ and $R^2$ independently is hydrogen, substituted or unsubstituted alkyl, substituted or unsubstituted cycloalkyl, or substituted or unsubstituted aryl, provided that not both $R^1$ and $R^2$ are hydrogen,
and each of x and y independently is an integer from 3 to 6.

In a preferred embodiment where discrete compounds are required, $R^1$ and $R^2$ are identical and x and y are identical.

Particularly preferred compounds are those wherein each of $R^1$ and $R^2$ is an alkyl group having from 5 to 8 carbon atoms, more preferably from 6 to 7 carbon atoms, and each of x and y is an integer from 3 to 6.

20 Claims, No Drawings

NON-IONIC SURFACE ACTIVE COMPOUNDS AND PHOTOGRAPHIC MATERIALS CONTAINING THEM

FIELD OF THE INVENTION

The invention relates to non-ionic surface active compounds. More particularly, the invention relates to certain 2-substituted N,N'-bis(D-glyconyl)propane-1,3-diamines.

PRIOR ART

U.S. Pat. No. 2 662 073-Mehltretten et al describes particular gluconamides possessing surface active properties. Because of their stability in alkaline solution and their ability to lower surface tension, some of the compounds are said to be of value as wetting agents in the textile industry. For example, they may be used in the mercerization of cotton and in the manufacture of viscose yarn. While a number of the gluconamides are insoluble in water, some of the branch chain compounds, e.g., N-2-ethylhexyl-gluconamide are said to be quite soluble.

There is a need for surface active compounds which, in addition to being water soluble, are more efficient at lowering surface tension and form micelles at lower concentrations than the gluconamides described in the above U.S. Pat. No. 2,662,073.

THE INVENTION

The surface active compounds of the invention may be used as dispersants, emulsifiers, wetting agents and coating aids. The compounds are photographically inactive and they are of particular use in the manufacture of photographic materials. They are especially useful in photographic compositions as coating aids to control coating unevenness or as dispersing aids to help obtain fine emulsions of hydrophobic materials in an aqueous medium.

The invention provides water soluble surface active compounds having the formula

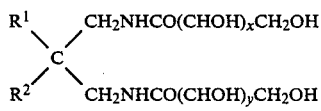

wherein each of $R^1$ and $R^2$ independently is hydrogen, substituted or unsubstituted alkyl, substituted or unsubstituted cycloalkyl, or substituted or unsubstituted aryl, provided that not both $R^1$ and $R^2$ are hydrogen, and each of x and y independently is an integer from 3 to 6.

In a preferred embodiment where discrete compounds are required, $R^1$ and $R^2$ are identical and x and y are identical.

Particularly preferred compounds are those wherein each of $R^1$ and $R^2$ is an alkyl group having from 5 to 8 carbon atoms, more preferably from 6 to 7 carbon atoms, and each of x and y is an integer from 3 to 6.

Preferred compounds in which $R^1$ and $R^2$ are other than alkyl possess a critical micelle concentration (CMC) as defined on page 83 et seq of "Surfactants and Interfacial Phenomena", M. J. Rosen, (1978), John Wiley & Sons, Inc. similar to those exhibited by the dialkyl derivatives described above, e.g. $<5 \times 10^{-3}$ moles/liter or $<0.3\%$ by weight in water.

The efficiency of the compounds at reducing the surface tension of an aqueous solution may be judged by measuring their $pC_{20}$ values as defined by Rosen on page 72 of the publication mentioned above. Preferred compounds of the invention have a $pC_{20}$ value greater than 3, more preferably greater than 4.

The surface active compounds may be used in the preparation of light sensitive photographic materials and the invention provides a photographic material comprising a support having thereon at least one layer comprising a hydrophilic colloid and such a compound.

MODES OF PRACTICING THE INVENTION

In the preparation of a photographic material, it is usual to coat a support with one or more layers comprising an aqueous solution of a hydropholic colloid binder e.g. gelatin. Such layers include, for example, silver halide emulsion layers, intermediate layers, antihalation layers, filter layers, antistatic layers and protective layers. For multilayer materials, the layers may be coated simultaneously on conventional photographic supports as described in U.S. Pat. Nos. 2,761,791 and 3,508,947.

In producing the thin hydrophilic colloid layers of such photographic materials, it is required that coating solutions are coated uniformly without the formation of repellency spots or craters, hereinafter referred to as repellencies. A repellency is a round, oval-shaped or comet-shaped indentation or crater in the layer of one or more of the layers coated and is usually produced by the presence of small particles or droplets of insoluble materials in the form of addenda, impurities or contaminants which are in contact with the uppermost liquid-air interface of the coated layer(s) and have surface activity (i.e. are capable of reducing the surface tension of the liquid-air interface during the coating process).

Solutions coated in the preparation of photographic materials often contain dispersed, insoluble photographic addenda, which might include organic solvents, or addenda to alter certain physical properties, which might include lubricants, each of which may be capable of imparting repellencies to the coated layer(s). Even photographic gelatin may contain insoluble residues of naturally-occurring animal fats and fatty acids which are capable of imparting repellencies to the coated layer(s). Also, surface active contaminants may originate from external sources during the preparation of the coating composition or during coating. For example, the layer(s) being coated, or immediately after coating, may be unintentionally showered by droplets of lubricating oils used in the apparatus.

In one aspect of the invention, a surface active compound of the invention is used as a coating aid in the formation of a hydrophilic colloid layer. Preferably, the coating aid is used in an amount from 0.01 to 0.30, more preferably from 0.05 to 0.20, weight % based on the weight of the hydrophilic colloid coating composition. The range of concentration within which the coating aid is used depends on the source of repellency. It also depends on whether other surface active agents are present.

A number of photographic additives used in light sensitive photographic materials are oil-soluble and are used by dissolving them in a substantially water-insoluble, high boiling point solvent which is then dispersed in a hydrophilic colloid aqueous solution with the aid of one or more dispersion agents. Such oil-soluble additives include image-forming dye couplers, dye stabilizers, antioxidants and ultra-violet radiation absorbing agents. Processes for dispersing oil-soluble photographic additives are well known in the art.

In another aspect of the invention, the surface active compound of the invention is used as a dispersion agent for dispersing oil-soluble photographic additives in a hydrophilic colloid aqueous solution.

The preferred hydrophilic colloid is gelatin e.g. alkali-treated gelatin (cattle bone or hide gelatin) and acid-treated gelatin (pigskin gelatin) or a gelatin derivative e.g. acetylated gelatin and phthalated gelatin. Other suitable hydrophilic colloids include naturally occurring substances such as proteins, protein derivatives, cellulose derivatives e.g. cellulose esters, polysaccharides e.g. dextran, gum arabic, zein, casein and pectin, collagen derivatives, agar-agar, arrowroot and albumin. Examples of suitable synthetic hydrophilic colloids include polyvinyl alcohol, acrylamide polymers, maleic acid copolymers, acrylic acid copolymers, methacrylic acid copolymers and polyalkylene oxides.

In the following discussion concerning the nature of the photographic material of this invention, reference will be made to Research Disclosure, December 1978, Item 17643, published by Industrial Opportunities Ltd., The Old Harbourmaster's, 8 North Street, Emsworth, Hants P010 7DD, U.K. This publication will be identified hereinafter as "Research Disclosure".

The material of this invention may comprise a negative-working or positive-working silver halide emulsion layer. Suitable emulsions and their preparation are described in Research Disclosure Sections I and II and the publications cited therein. Suitable vehicles for the emulsion layers and other layers of elements of this invention are described in Research Disclosure Section IX and the publications cited therein.

For colour photographic materials, references giving information on couplers and on methods for their dispersions are given in Sections VII and XIV, respectively, of Research Disclosure. An account of dye-forming development is given in 'Modern Photographic Processing', Vol. 2, Grant Haist, Wiley, New York, 1978, Chapter 9.

The photographic materials of this invention or individual layers thereof, can contain brighteners (see Research Disclosure Section V), antifoggants and stabilizers (see Research Disclosure Section VI), antistain agents and image dye stabilizer (see Research Disclosure Section VII, paragraphs I and J), light absorbing and scattering materials (see Research Disclosure Section VIII), hardeners (see Research Disclosure Section XI), plasticizers and lubricants (see Research Disclosure Section XII), antistatic agents (see Research Disclosure Section XIII), matting agents (see Research Disclosure Section XVI) and development modifiers (see Research Disclosure Section XXI).

The photographic materials can be coated on a variety of supports as described in Research Disclosure Section XVII and the references described therein.

The photographic materials can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a colour developing agent to reduce developable silver halide and oxidize the colour developing agent. Oxidized colour developing agent in turn reacts with the coupler to yield a dye.

With negative working silver halide emulsions this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

The 2-substituted N,N'-bis(D-glyconyl)propane-1,3-diamines may be prepared using malononitrile as the starting material. This may be substituted with groups corresponding to $R^1$ and $R^2$ according to known procedures. For example, malononitrile may be dialkylated by the method described by J. J. Bloomfield, J. Org. Chem. 1961, 26, 4112. The intermediate dinitrile is then reduced to the diamine with lithium aluminium hydride using, for example, the method described in Org. React. 1951, 6, 469.

The resulting diamine may be treated with the appropriate carbohydrate lactone to yield the desired compound. In a typical preparation, a diamine and two molar equivalents of a carbohydrate lactone were heated together under reflux in methanol for up to 24 hours. Upon cooling to room temperature, the product crystallizes out of solution. Alternatively, when x and y are 4, the diamine may be treated with two molar equivalents of penta-O-acetyl glyconylchloride and triethylamine in tetrahydrofuran (Org. Synth. Coll., Vol. V, 887). Subsequent deacetylation of this intermediate gives the required compound.

The amides may be purified by treatment with a cation exchange resin to remove unreacted amine and unwanted side product. A detailed description of the preparation of a compound of the invention is given below.

Preparation of
2,2-(Dihexyl)-N,N'-bis(D-ribonyl)-propane-1,3-diamine (1a) and
2,2-(Dihexyl)-N,N'-bis(D-gluconyl)propane-1,3-diamine (1b)

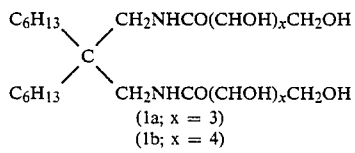
(1a; x = 3)
(1b; x = 4)

2,2-Dihexylpropanedinitrile

Malononitrile (5.98 g, 90 mmol) dissolved in dry DMSO (20 ml) was added to a mechanically stirred slurry of sodium hydride (4.36 g, 0.18 mol) in dry DMSO (60 ml) under a nitrogen atmosphere. The stirring was continued for 15 min and then 1-bromohexane (30.0 g, 0.18 mol) was added over a period of 1 h with occasional cooling of the reaction flask in an ice bath. During the addition the reaction mixture became very viscous and difficult to stir. Toluene (150 ml) was added to dilute the reaction mixture and make stirring easier.

After stirring at room temperature for 3.5 h, the reaction mixture was poured into ice/water (1500 ml) and stirred for 1 h. The mixture was extracted with diethyl ether and the ether layer was separated, dried over anhydrous magnesium sulphate and evaporated to yield a yellow oil. The oil was distilled under reduced pressure to yield 2,2-dihexylpropane-dinitrile as a colorless oil (9.0 g, 42.5%) b.p. 136°–137° C./1.0 mm (Found: C, 77.4; H, 11.3; N, 12.55; $C_{15}H_{26}N_2$ requires C, 76.9; H, 11.1; N, 12.0%).

2,2-Dihexylpropane-1,3-diamine 2,2-Dihexylpropanedinitrile (22.0 g, 94 mmol) dissolved in dry diethyl ether (100 ml) was added slowly to a suspension of lithium aluminium hydride (8.7 g, 0.23 mol) in dry diethyl ether (250 ml) under nitrogen. Upon complete addition, the mixture was heated under reflux using a water bath for 1 h and then stirred at room temperature for 24 h. Water was carefully added to the reaction mixture with cooling of the flask in an ice bath, until no more hydrogen was evolved. The reaction mixture separated into two layers and the ether layer was decanted from the aqueous layer, washed with water, and dried with anhydrous magnesium sulphate. The ether was evaporated to yield a viscous oil that was distilled under reduced pressure to yield 2,2-dihexylpropane-1,3-diamine as a colorless liquid (11.2 g, 49%) b.p. 138°–142° C./0.7 mm.

2,2-(Dihexyl)-N,N'-bis(D-ribonyl)propane-1,3-diamine (1a)

2,2-Dihexylpropane-1,3-diamine (4.5 g, 18 mmol) and 1,4-D-ribonolactone (5.5 g 36 mmol) were heated together under reflux in methanol (150 ml) for 24 h. Upon cooling to room temperature a weakly acidic ion exchange resin (Amberlite IRC50, 10.0 g) was added and the mixture was stirred for a further 24 h. The mixture was then filtered and the methanol evaporated to yield a sticky yellow solid. This was recrystallized three time from acetone to give 2,2-(dihexyl)-N,N'-bis-(D-ribonyl)propane-1,3-diamine as an amorphous solid (4.0 g, 40%) m.p. 144°–146° C. (Found: C, 53.3; H, 9.1; N, 5.2; $C_{25}H_{50}N_2O_{10}.1.5H_2O$ requires C, 53.1; H, 9.4; N, 5.0%).

2,2-(Dihexyl)-N,N'-bis(D-gluconyl)propane-1,3-diamine (1b)

2,2-Dihexylpropane-1,3-diamine (11.0 g, 45 mmol) and 1,5-D-gluconolactone (16.2 g, 90 mmol) were heated under reflux in methanol (300 ml) for 6 h. Upon cooling to room temperature, a solid crystallized from solution. This was quickly filtered off, recrystallized from methanol and dried in a vacuum oven at 50° C. to give 2,2-(Dihexyl)-N,N'-bis(D-gluconyl)propane-1,3-diamine as colorless crystals (12.1 g, 44.5%) m.p. 179° C. (Found: C, 52.8; H, 9.0; N, 4.6; $C_{27}H_{54}N_2O_{12}.H_2O$ requires C, 52.6; H, 9.1; N, 4.5%).

The compounds of the invention are readily obtained in pure form.

The invention is further illustrated with reference to the following Examples.

The compounds used in the Examples are defined having regard to the following general formula:

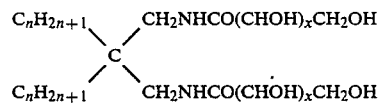

EXAMPLE 1

The efficiency of compounds of the invention as surface active agents was assessed by measuring their critical micelle concentration (CMC) in water and by measuring the weight of surface active agent required to lower surface tension by 20 mN/m as defined by Rosen, "Surfactants and Interfacial Phenomena", published by Wiley 1978 (pages 153–159).

For comparison, the same measurements were made using 2-ethylhexylgluconamide.

The results are shown in Table 1.

TABLE 1

| Compound | CMC wt % (moles/l) | Wt % (moles/l) to lower surface tension by 20 mN/m |
|---|---|---|
| n = 6, x = 3 | 0.08 (1.4 × $10^{-3}$) | 0.002 (3.4 × $10^{-5}$) |
| n = 6, x = 4 | 0.1 (1.6 × $10^{-3}$) | 0.003 (5.0 × $10^{-5}$) |
| n = 7, x = 5 | 0.013 (2.0 × $10^{-4}$) | 0.0003 (4.5 × $10^{-6}$) |
| 2-ethylhexyl gluconamide | 3.0 (1.0 × $10^{-1}$) | 0.26 (8.5 × $10^{-3}$) |

The above data clearly show that the compounds of the invention are far more efficient at reducing surface tension or in forming micelles than 2-ethylhexyl gluconamide.

EXAMPLE 2

A repellency is a coating unevenness such as a round, oval, or comet-shaped indentation or crater in layered materials. The ability of a compound of the invention to control repellencies arising from a source of surface active material within a coating composition was tested as follows.

Two gelatin layers, the uppermost of which contained a compound of the invention as a coating aid, were coated onto a polyethylene terephthalate film base suitably subbed to give good adhesion to gelatin. The bottom layer consisted of a 4% by weight solution of a bone gelatin in water coated at 85.4 ml/m². The top layer consisted of a 7% by weight solution of a bone gelatin in water containing a colored dye marker, 1 ppm oleic acid as a contaminant to induce repellency and a quantity of the surface active compound under test. The top layer was applied at a coverage of 14.2 ml/m². Both layers were applied simultaneously at a temperature of 40° C. using a conventional double slide hopper with applied suction and a linear coating speed of 15 m/min.

For each series of experiments, the coating aid was used in amounts ranging from 0.05 to 0.30% by weight based on the weight of the coating solution for the top layer.

By way of comparison, the experiment was repeated using 2-ethylhexyl gluconamide as the coating aid.

The results are summarized in Table 2.

TABLE 2

| Concentration (coating aid) wt % | Compounds | | | |
|---|---|---|---|---|
| | 2-Ethylhexyl gluconamide (Comparison) | n = 6, x = 4 | n = 7, x = 4 | n = 7, x = 5 |
| 0.05 | — | R | C | C |

TABLE 2-continued

| | Compounds | | | |
|---|---|---|---|---|
| Concentration (coating aid) wt % | 2-Ethylhexyl gluconamide (Comparison) | n = 6, x = 4 | n = 7, x = 4 | n = 7, x = 5 |
| 0.10 | R | C* | C | C |
| 0.15 | R | C | — | — |
| 0.20 | R | C | — | — |
| 0.25 | R | C | — | — |
| 0.30 | R | C | — | — |

In Table 2, R denotes that the coating was covered in large numbers of repellencies while C denotes that no repellencies were produced, i.e. complete control of repellencies. C* denotes virtual control of repellencies i.e. only occasional single repellencies were observed, of the order of one or two per meter.

We claim:

1. A water soluble surface active compound having the formula

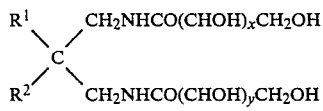

wherein
each of $R^1$ and $R^2$ independently is hydrogen, substituted or unsubstituted alkyl, substituted or unsubstituted cycloalkyl, or substituted or unsubstituted aryl, provided that not both $R^1$ and $R^2$ are hydrogen,
and each of x and y independently is an integer from 3 to 6.

2. A compound according to claim 1 wherein each of $R^1$ and $R^2$ is an alkyl group having from 5 to 8 carbon atoms and each of x and y is an integer from 3 to 6.

3. A compound according to claim 2 wherein each of $R^1$ and $R^2$ is an alkyl group having 6 or 7 carbon atoms.

4. The compound of claim 1 wherein $R^1$ and $R^2$ are identical.

5. The compound of claim 4 wherein x and y are identical.

6. A photographic material comprising a support having thereon at least one layer comprising a hydrophilic colloid and a surface active compound, characterized in that the surface active compound is a compound having the formula

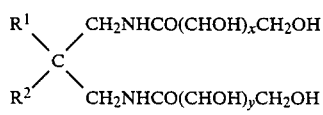

wherein
each of $R^1$ and $R^2$ independently is hydrogen, substituted or unsubstituted alkyl, substituted or unsubstituted cycloalkyl, or substituted or unsubstituted aryl, provided that not both $R^1$ and $R^2$ are hydrogen,
and each of x and y independently is an integer from 3 to 6.

7. The photographic material according to claim 6 wherein each of $R^1$ and $R^2$ is an alkyl group having from 5 to 8 carbon atoms and each of x and y is an integer from 3 to 6.

8. The photographic material according to claim 6 wherein each of $R^1$ and $R^2$ is an alkyl group having 6 or 7 carbon atoms.

9. The photographic material according to claim 6 wherein $R^1$ and $R^2$ are identical.

10. The photographic material according to claim 9 wherein x and y are identical.

11. A process for preparing a photographic material wherein an aqueous coating solution comprising a hydrophilic colloid and a coating aid is coated as a layer of the material, characterized in that the coating aid is a water soluble surface active compound having the formula

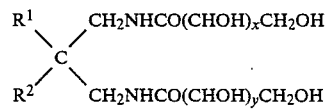

wherein
each of $R^1$ and $R^2$ independently is hydrogen, substituted or unsubstituted alkyl, substituted or unsubstituted cycloalkyl, or substituted or unsubstituted aryl, provided that not both $R^1$ and $R^2$ are hydrogen,
and each of x and y independently is an integer from 3 to 6.

12. The process according to claim 11 wherein each of $R^1$ and $R^2$ is an alkyl group having from 5 to 8 carbon atoms and each of x and y is an integer from 3 to 6.

13. The process according to claim 12 wherein each of $R^1$ and $R^2$ is an alkyl group having 6 or 7 carbon atoms.

14. The process according to claim 11 wherein $R^1$ and $R^2$ are identical.

15. The process according to claim 14 wherein x and y are identical.

16. A process for preparing a photographic coating composition which comprises dispersing an oil soluble photographic additive in an aqueous solution of a hydrophilic colloid in the presence of a dispersion aid, characterized in that the dispersion aid comprises a water soluble surface active compound having the formula

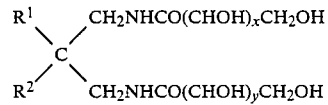

wherein
each of $R^1$ and $R^2$ independently is hydrogen, substituted or unsubstituted alkyl, substituted or unsubstituted cycloalkyl, or substituted or unsubstituted aryl, provided that not both $R^1$ and $R^2$ are hydrogen,
and each of x and y independently is an integer from 3 to 6.

17. The process according to claim 16 wherein each of $R^1$ and $R^2$ is an alkyl group having from 5 to 8 carbon atoms and each of x and y is an integer from 3 to 6.

18. The process according to claim 17 wherein each of $R^1$ and $R^2$ is an alkyl group having 6 or 7 carbon atoms.

19. The process according to claim 16 wherein $R^1$ and $R^2$ are identical.

20. The process according to claim 19 wherein x and y are identical.

* * * * *